(12) United States Patent
Arlemark (10) Patent No.: US 9,233,182 B2
(45) Date of Patent: Jan. 12, 2016

(54) MOBILE DISINFECTION UNIT FOR DISINFECTING A GIVEN FACILITY OR EQUIPMENT AND A METHOD OF USING SAID UNIT

(71) Applicant: O3 TECHNOLOGY RESEARCH & DEVELOPMENT AB, Vellinge (SE)

(72) Inventor: Jan Arlemark, Loulé (PT)

(73) Assignee: O3 Technology Research & Development AB, Vellinge (SE)

( * ) Notice: Subject to any disclaimer, the term of this patent is extended or adjusted under 35 U.S.C. 154(b) by 0 days.

(21) Appl. No.: 14/374,800

(22) PCT Filed: Jan. 25, 2013

(86) PCT No.: PCT/EP2013/051493
§ 371 (c)(1),
(2) Date: Jul. 25, 2014

(87) PCT Pub. No.: WO2013/110782
PCT Pub. Date: Aug. 1, 2013

(65) Prior Publication Data
US 2015/0017059 A1 Jan. 15, 2015

(30) Foreign Application Priority Data
Jan. 26, 2012 (EP) .................................. 12152733

(51) Int. Cl.
*A61L 2/20* (2006.01)
*A61L 2/24* (2006.01)
(Continued)

(52) U.S. Cl.
CPC ... *A61L 2/24* (2013.01); *A61L 2/03* (2013.01); *A61L 2/10* (2013.01); *A61L 2/202* (2013.01); *A61L 9/015* (2013.01); *A61L 2202/16* (2013.01); *A61L 2202/25* (2013.01)

(58) Field of Classification Search
CPC ........................................................ A61L 2/202
USPC .......................................................... 422/3, 28
See application file for complete search history.

(56) References Cited

U.S. PATENT DOCUMENTS 3,633,262 A * 1/1972 Van Huffel et al. .......... 29/592.1
4,776,864 A * 10/1988 Werner ............................. 96/55
(Continued)

FOREIGN PATENT DOCUMENTS

GB 2468641 A 9/2010
GB 2472509 A 2/2011
(Continued)

OTHER PUBLICATIONS

International Search Report and Written Opinion, PCT/EP2013/051493, mailed Jun. 28, 2013.

*Primary Examiner* — Sean E Conley
*Assistant Examiner* — Donald Spamer
(74) *Attorney, Agent, or Firm* — Winston & Strawn LLP (57) ABSTRACT

A mobile disinfection unit for use in a method of disinfecting a given facility or equipment such as a room, apparatus, container or vehicle. The unit includes a catalytic converter device for decomposing ozone, a VOC filter for removing bacterial viruses and other contaminants and an electrostatic filter for removing molecules, particles, droplets, smoke and dust. The method includes a treatment step for adding ozone and steam/water droplets into the air of the facility or equipment, a detection step of continuously detecting the ozone concentration in the facility or equipment, and a removal step arranged for removing residual ozone and any contaminates from the facility or equipment when a predefined ozone concentration has been reached and maintained for a specific time interval.

18 Claims, 3 Drawing Sheets

(51) Int. Cl.
  *A61L 9/015* (2006.01)
  *A61L 2/03* (2006.01)
  *A61L 2/10* (2006.01)

(56) References Cited

U.S. PATENT DOCUMENTS

| | | | |
|---|---|---|---|
| 7,604,774 B2 | 10/2009 | Mole et al. | |
| 2005/0189210 A1* | 9/2005 | Uslenghi et al. | 204/157.3 |
| 2006/0263276 A1* | 11/2006 | Pattee | 422/186.07 |
| 2008/0196723 A1* | 8/2008 | Tilley | 128/204.23 |
| 2008/0310992 A1* | 12/2008 | Heselton et al. | 422/2 |
| 2009/0010801 A1 | 1/2009 | Murphy et al. | |
| 2010/0254868 A1 | 10/2010 | Obee et al. | |
| 2011/0033346 A1 | 2/2011 | Bohlen et al. | |

FOREIGN PATENT DOCUMENTS

| | | |
|---|---|---|
| WO | WO 2008/014615 A1 | 2/2008 |
| WO | WO 2009/002295 A1 | 12/2008 |

\* cited by examiner

MOBILE DISINFECTION UNIT FOR DISINFECTING A GIVEN FACILITY OR EQUIPMENT AND A METHOD OF USING SAID UNIT

This application is a 371 filing of International Patent Application PCT/EP2013/051493 filed Jan. 25, 2013, which claims the priority of European patent application no. 12152733.7 filed Jan. 26, 2012.

BACKGROUND

The present invention relates to a method for disinfecting a given facility or equipment such as a room, apparatus, container or vehicle, and a mobile disinfection unit for use in the method.

It is well known that facilities of different kind such as rooms, containers or vehicles can be infected or contaminated with different chemicals, spores or viruses. These infections or contaminants are detrimental to the health and the quality of life. So far the technology is mainly based on manual cleaning, which is time consuming and expensive and which further contains the risk of cross contamination during the cleaning period.

Several attempts have been made in order to meet this problem, however presently, there is not an integrated system available for cleaning and disinfecting hospital rooms, where also nanoparticles can be removed to a high extend. Nanoparticles are present in all environments, and are also likely to be formed from different gases in the air after being oxidized by ozone. Terpines for example form nanoparticles when oxidized, and many are cancerogenic. Also, in hospitals and anesthesia many of the inhaled gases and its residuals contain components harmful for the health and environment.

UV light is used in hospitals to sterilize the air, but the method only removes very few specific types of pollution, and furthermore does not create enough radiation to remove bacteria and spores within an acceptable time. Chemical treatment is hazardous for the personnel and by mechanical filtration the pollution particles are only collected on a screen. Mechanical filtration is equal to high pressure loss. The filter must be changed and can itself become a source of bacterial contamination. In contrast electrostatic filtration does not cause a large pressure drop, and removes pre-existing particles. Electrostatic filtration does, however, not act on gas-phase pollution.

Ozone in combination with humidity is known to have a rapid effect on spores, viruses and bacteria. Ozone is further one of the strongest oxidizing agents known to mankind. During ozone treatment a lot of the substances in air are being oxidized resulting in nanoparticle byproducts directly able to penetrate the respiratory system, or to have health or environmental effects.

To remedy the above disadvantages different modifications and variations of disinfection and sterilization methods have been proposed. Examples include the methods and apparatuses of Steritrox Limited in the patent application GB2468641 and the U.S. Pat. No. 7,604,774. The sterilization method presented in GB2468641 aim at sterilization, decontamination and/or sanitation of a cool environment e.g. a food preparation area. The method describes the steps of measuring the temperature of an enclosed environment to be treated, calculating the relative humidity, introducing humidity to the environment, introducing ozone to the humidified environment, maintaining a predetermined concentration of ozone in the environment, and finally removing the ozone from the environment again after the aimed degree of sterilization has been obtained. In case removal of the ozone takes too much time, the ozone level may be reduced by introducing a hydrocarbon gas containing a carbon-carbon double bond into the environment. The sterilization method presented by Steritrox Limited in U.S. Pat. No. 7,604,774 is much similar to GB2468641, however comprising the step of introducing an aromatic hydrocarbon into the humidified environment after introducing ozone to preferentially react with said discharged ozone to form hydroxyl radicals. The Steritrox documents do thus not let the apparatus collect the produced contaminants and decompose the contaminants in a filter. Furthermore, in the U.S. Pat. No. 7,604,774 the apparatus does not collect and decompose the residual ozone in a catalyst. Also, it is not considered how to remove toxic gaseous contaminants and particles such as smoke and dust from the air.

WO 2008/014615 A1 discloses a method of sterilizing a closed environment such as hotels, airplanes, cruise ships and hospitals, and a disinfection apparatus to be used in the method. The method of sterilization is among others aimed against SARS, influenza virus, poliovirus and rhinovirus. The method comprises the steps of placing the disinfection apparatus in the closed environment, having the apparatus generate ozone in the closed environment to a predetermined ozone concentration, rapidly increasing the humidity in the closed environment to a predetermined level, and guiding the air in the closed environment through a catalytic converter so that the ozone concentration is reduced to a predetermined safe level, at which stage the disinfection apparatus signals that the closed environment is safe to enter. The predetermined ozone concentration is stated to be within 15 to 40 ppm, or 20 to 30 ppm, and may be depleted with a catalytic converter and by guiding ozonated air through a manganese dioxide and activated carbon tray. The humidity in said closed environment may be raised to levels higher than 90% by use of an ultrasonic humidifier. The disinfection apparatus may further comprise e.g. an ozone sensor, and a first fan to guide ozonated air into the catalytic converter. However, WO 2008/014615 A1 does only provide one inlet tube, so that intake of air to the apparatus happens through the same inlet tube during both the initial introduction of ozone to the environment and the final reduction of ozone. The processes cannot be separated, which complicates the design of the apparatus and wears more on the apparatus. GB 2 472 509 A and US 2009/010801 A1 also present air cleaners comprising more than one means of cleaning such as an ozone depletion unit, VOC filter and electrostatic filter. They do, however, not provide an alternative design in regard to the inlet tube, but also only have one inlet tube.

Known methods for sterilizing/disinfecting a given facility thus result in an incomplete and complicated process. Thus, improvements over the prior art are desired.

SUMMARY OF THE INVENTION

It is a first aspect of the present invention to provide a disinfection method of the kind mentioned in the opening paragraph that is simple to operate.

It is a second aspect of the present invention to provide a disinfection method of the kind mentioned in the opening paragraph that produces a complete disinfection of the facility or equipment.

It is a third aspect of the present invention to provide a disinfection method of the kind mentioned in the opening paragraph that is safe to use.

It is a fourth aspect of the present invention to provide a disinfection method of the kind mentioned in the opening paragraph that gives a fast disinfection process.

It is a fifth aspect of the present invention to provide a disinfection method of the kind mentioned in the opening paragraph that has a relatively low energy consumption.

It is a sixth aspect of the present invention to provide a mobile disinfection unit, which facilitates the method according to the present invention.

It is a seventh aspect of the present invention to provide an alternative to the disinfection methods mentioned in the opening paragraph.

The novel and unique features whereby these and other aspects are achieved according to the invention consists in the fact that the method comprises a treatment step arranged for adding ozone and steam and/or water droplets into the air of the facility or equipment, means for continuously detecting the ozone concentration in the facility or equipment, and a removal step arranged for removing residual ozone and any contaminates from the facility or equipment, when a predefined ozone concentration has been reached and maintained for a specific time interval.

One huge advantage of applying these two separated steps, while simultaneously detecting the ozone concentration in the facility or equipment is that progress of the treatment step can be monitored by the means for detecting the ozone concentration. The monitoring effect means that the different parameters of the treatment step, e.g. ozone and steam/water droplets concentrations, can be traced and adjusted according to their progress, and that a predefined ozone concentration can be reached and maintained for a specific time interval. The monitoring effect also means that the treatment step can be controlled not to be terminated prematurely before the contaminants have been completely removed. Having a removal step secures that residual ozone and any additional contaminants will be removed completely from the facility or equipment after the treatment step and thus not leave any products from the treatment process none-decomposed.

The term "contaminant" means within the context of the present invention any undesirable components present in the facility or equipment, and will encompass both end- and by-products present after the treatment step as well as inorganic material, such as carbon monoxide and cigarette smoke, organic compounds such as pollen, as well as living organisms such as viruses, spores and bacteria.

Advantageously, the method further comprises means for continuously detecting an additional parameter in the facility or equipment, said parameter is selected from the group of temperature, relative humidity, concentration of one or more contaminants, or a combination of said parameters. Having said means facilitates better control of the entire disinfection process, i.e. that the single steps in the disinfection process can be controlled and adjusted continuously and optionally automatically, dependent on the parameter detected by the means.

The means for detecting said additional parameter will depend on the relevant parameter, however such detection means are well known in the art.

The treatment process can preferably comprise the individual steps of first continuously circulating the air in the facility or equipment from a first inlet opening to a first outlet opening. Then the mixture of ozone and steam/water droplets can advantageously be formed by producing steam and/or water droplets and adding the steam and/or water droplets to the flow of air, for e.g. facilitating the formation of hydroxyl radicals, followed by producing and mixing ozone molecules with the steam and/or water droplets in the flow of air. By forming the mixture in the flow of air before expelling it to the facility or equipment helps to secure that a homogenous mix between the ozone and the steam and/or water droplets has been formed. Optionally, the mixture can be added negative ions or electrical charge, before the mixture is released to the facility or equipment.

In a preferred embodiment the method comprises calculating the necessary treatment time. The treatment time can e.g. be dependent on the increase in the ozone concentration. In one example can the concentration of the steam/water droplet and ozone concentrations be increased or decreased in order to meet the calculated treatment time, or alternatively can the treatment time be adjusted if the predefined ozone level cannot be reached. In this way it is possible to ensure optimal disinfection conditions.

After the treatment time has elapsed the production and release of steam/water droplets and ozone to the facility or equipment is stopped thus terminating the treatment process.

It is preferred that any ventilation or other airflow between the facility to be disinfected and other faculties are closed before and during execution of the method according to the invention, in order to ensure that ozone used in the method according to the invention is not spread to other facilities.

Advantageously, a relative humidity (R.H.) level above 50% at room temperature can be applied. High levels of relative humidity, R.H>50%, helps particles to conglomerate and by having a high relative humidity together with ozone at a predetermined level a rapid disinfection takes place. The humidity can e.g. be obtained simply by addition of the mixture of ozone and steam and/or water droplets and if said humidity is not sufficient be created with miniature spray nozzles (e.g. foggers), or through high frequency shakers or by generating heat and steam by temperature. The humidity may be adjusted dependent on the specific type of contaminant. If the contamination mainly comprises viruses, spores or bacteria the humidity may preferably be 40%, 75-80% or 65%, respectively.

The humidity present in the facility after completion of the method according to the invention can in a preferred embodiment be recovered by means of a dehumidifier and be reused in the method according to the invention. In a different embodiment said humidity is simply left in the facility or equipment and can be removed by means of e.g. a ventilation system og climate system already present in the facility or equipment.

In principle any source of ozone may be used provided the ozone can be delivered or generated in the desired amounts and in a safe way.

In a preferred embodiment the ozone source can be an ozone generator as for example a corona discharge generator. Electric corona discharge generators produce large quantities of ozone in an economical way. Ozone can also be generated using UV light although this is too inefficient and expensive at present. However, should the technology advance for generating ozone using UV or other methods, it may be incorporated into the present invention. Ozone can alternatively be produced through electrolysis.

In any way for said reason a corona discharge ozone generator is the preferred method. The passage of a high voltage, alternating electric current through an air stream containing oxygen breaks down molecular oxygen into atomic oxygen. These oxygen atoms may react to form ozone. Commercial ozone generators are available in various shapes and sizes with various capacities for generating ozone. In another preferred embodiment the ozone source can be an ozone generator from O3-Technology AB, which is based on a technology wherein oxygen or air is passed through a corona discharge tube or through parallel plates, and a charge is maintained by an AC voltage by medium frequency. The amount of ozone is made by drive train of pulses in combination with regulating the voltage. This unit will produce the majority of the ozone in the system/reactor. Ozone oxidizes most or all organic compounds such as aromatic- and unsaturated-hydrocarbons. However, many kinds of compounds/chemicals, such as saturated hydrocarbons and material trapped in the liquid or solid phases of aerosols, may or may not react with ozone. Other air pollutants that may not react with ozone include carbon monoxide, pollen and cigarette smoke.

The ozone acts as a biocide killing biological material, such as bacteria, moulds and spores in the air or on surfaces. Ozone is a naturally occurring substance which cleans air and removes odors from air. The photochemical oxidation by $O_3$, OH and other species in the reaction region will mainly result in additional oxygen containing functional groups (e.g. alcohols, carbonyls, acids, etc.) on organic pollution molecules. Each functional group will reduce the vapor pressure of the organic molecule increasing its propensity for forming aerosols.

At the high relative humidity typically above R.H. 50% ozone and water react, thus forming highly reactive ozone-based free radical intermediates, such as hydroxyl radicals, that in turn react with and neutralize airborne pathogens as well as pathogen on all surfaces.

Presence of water vapor initially breaks down the ozone, into oxygen ($O_2$) and an electronically excited oxygen atom (O*) also termed an oxygen radical. The excited oxygen radical may react with organic material (moisture) in the air and form hydroxyl radicals $$O^*+H_2O=2.OH$$

Furthermore, the excited oxygen radical may react with a hydrocarbon or with an oxygen molecule to reform ozone $$O_3+h\nu=O_2+O^*$$

$$O^*+H_2O=2\times.OH$$

$$O^*+RH=.OH+R^*$$

$$O^*+M=O+M$$

$$O+O_2+M=O_3+M$$

where hν is a photon with a wavelength below 330 nm
.OH is a hydroxyl radical,
RH is a hydrocarbon,
M is a collision partner, usually $N_2$ or $O_2$, and
O* is an excited oxygen molecule.

Hydrocarbon radicals may react by addition or fragmentation to obtain aldehydes, ketones, acids, alcohols or other functionalized hydrocarbons.

Thus in the treatment zone, some of the ozone will be broken down into oxygen gas and hydroxyl radicals. It will also be recognized by those skilled in the art that hydroxyl radicals can form peroxides, which themselves can act as biocides. Therefore, these peroxides, in addition to the hydroxyl radicals, assist in killing any living biological material, which may enter or be present in the treatment zone. Hydrocarbons may react with hydroxyl radicals:

$$CH_4+{}^*OH={}^*CH_3O_2+M$$

$$CH_3+O_2+M=CH_3O_2+M$$

$$CH_3O_2+NO=CH_3O+NO_2$$

$$CH_3O+O_2=CH_2O+HO_2$$

NO is present in the background air. Any kind of hydrocarbon will make an oxy radical like the methoxy radical above, and this radical can donate an H to $O_2$ to form a stable aldehyde/ketone and .HO Another source of $H_2O_2$ will be:

$${}^*HO_2+{}^*HO_2=H_2O_2+O_2$$

Ozone in combination with humidity, which may form hydroxyl radicals and/or peroxides, destroys microorganisms which are not killed by the ozone itself. The free radicals formed by the interaction of ozone with water in the treatment zone act as an oxidant on cell walls even before they penetrate inside the microorganisms where they oxidize essential components such as enzymes and proteins.

Ozone does react significantly with either water or oxygen. Water and air merely provide the medium in which ozone diffuses to react with organic molecules such as those on the outside of the cell wall of pathogens such as bacteria, viruses, moulds or pollen. Ozone and water add to decomposition into various highly reactive free radicals, such as hydroxyl radicals.

The treatment time can be calculated from the curve of ozone built up in the air to ensure the necessary treatment time, defined as the time from where the ozone concentration has reached its predefined value. It is possible depending on the circumstances and the facility or equipment to be cleaned/disinfected, to have a low ozone concentration for a long period of time or a high ozone concentration for a short period of time, the only requirement is that the ozone concentration and time said concentration is present in the facility or equipment is set such that the contaminants are decomposed. As an example can be mentioned that if the ozone concentration is 15 parts per million (ppm) said concentration has to be maintained in the facility or equipment for a period of 45 minutes to 1 hour for a sufficient decomposing to take place.

An important feature of the inventive method is that an aerosol growth zone is provided through water and ozone. The purpose of this step is to allow particles to grow, removing pollution from the gas phase. The treatment time should thus be set to ensure sufficient retention time for aerosol growth.

One problem by traditional air purification is that smells or odors cannot be removed, even by ozone. However, due to the use and formation of —OH, other radicals derived from ozone or other sources, smells and odors can be removed.

The necessary treatment time depends on various factors including the type of contamination the apparatus is exposed to during the treatment, the ozone source, the temperature, the volume of the room to be treated and the level of total impurities. If the content of organics increase in the system the generator may increase the concentration to be able to treat the air in the expected time. The apparatus will automatically set for a longer treatment time should it find the predefined level of ozone is hard to reach. Based on the required flow rates in the system and the dimensions of the room/facility/equipment, the treatment time should typically be less than 30 minutes, preferably less than 20 minutes, most preferably less than 10 minutes.

Following the treatment process the removal process can be initiated. The removal process can preferably comprise the individual steps of first continuously circulating the air in the facility or equipment from a second inlet opening to a second outlet opening. In order to remove the residual ozone the inlet air flow is exposed to a catalytic converter device comprising one or more ozone removal catalysts. The catalytic converter device provides a means for removing the residual ozone thus avoiding the risk of exposing e.g. personnel to a hazardous ozone concentration when the personnel enters the facility after the disinfection process has been completed.

In order to ensure that the air in the facility or equipment is completely cleaned the air can preferably also be exposed to a Volatile Organic Compounds (VOC) filter composed of Titanium dioxide irradiated with Ultra Violet (UV) radiation for removal of bacterial viruses and other contaminants which has not been removed or decomposed after the ozone treatment in the treatment process. If any molecules, particles and droplets still remain after the VOC-filter, these can be exposed to electrostatic plates, providing said remaining molecules, particles and droplets with an electric charge, which secures removal in an electrostatic precipitator. Any final remaining smaller particles can be removed in an electrostatic filter comprising charged metallic plates.

A catalyst converter device for removal of residual ozone can be very important, since prolonged exposure to elevated concentrations of ozone may irritate the respiratory system and harm the lungs. The U.S. Environmental Protection Agency classifies average 8-hour exposures of 85 to 105 parts per billion (ppb) as unhealthy for sensitive groups. Concentrations higher than this increase the risks. It is therefore preferred that the ozone concentration is reduced to an ozone concentration below these levels and at least below <0.1 ppm before the removal process is completed.

The catalyst converter device can comprise one or more ozone removal catalysts known in the art. Ozone removal catalysts that can be used include manganese dioxide, all-aluminum catalysts, a carbon-supported metal oxide, copper, chloride-coated carbon fibers, carbon-iron aerosol particles, and metal catalysts. CARULITE® (an inorganic oxide) made by Carus Chemical Company is another ozone removal catalyst. The catalyst may be solid-supported, and any solid support may be used, preferably glass or silica. The catalyst can also comprise manganese dioxide containing paint.

The catalyst for removal of residual ozone preferably have a large surface area for contacting the air containing the residual ozone.

The unstable and highly reactive free radical intermediates obtained from ozone, e.g. hydroxyl radicals, form stable products including water and carbon dioxide that are not associated with health risks when present in air at small concentrations. The decomposition of ozone into stable oxygen is accelerated by surfaces that act as substrates and/or reaction-sites for the decomposition process.

The remaining flow of gas is passed through a VOC filter, where the airflow preferably should be at a velocity at or below 2 m/sec.

The air leaving the decomposition of ozone can be subjected to a source (e.g. electrostatic plates) providing the molecules, particles and droplets with an electrical charge enabling their removal with an electrostatic filter. In a preferred embodiment the electrical charge is DC voltage. The charged molecules, particles and droplets will afterwards be attracted to the counter pole plate in the precipitator. It is preferred that the velocity of the inlet air is brought down below 2 m/sec, more preferred below 1.5 m/sec and even more preferred the speed is 1 m/sec.

It may be that charging the particles will improve aerosol particle trapping, because the agglomeration of oppositely charged particles will increase particle size, and the presence of charge will improve the thermodynamics of particle growth. Heavier combined particles may precipitate (fall) out of the air when two smaller particles agglomerate.

Any electrostatic precipitator can be used in the present invention. An electrostatic precipitator is a particulate collection device that removes particles from a flowing gas (such as air) using the force of an induced electrostatic charge. Electrostatic precipitators are highly efficient filtration devices that minimally impede the flow of gas and can efficiently remove fine particulate matter such as smoke or dust from the air stream.

Smaller particles, which are not heavy enough to precipitate, are forced out through electrostatic filtration. The electrostatic filtration comprises charged metal plates, with alternating positive and negative charges, where positive aerosol-particles will accelerate into the negative plates and negative aerosol-particles will accelerate into the positive plates. The addition of moisture, ammonia and/or other agents to the incoming air improves the efficiency of trapping pollution and pollution oxidation products through the mechanism of aerosol growth.

The time of electrostatic precipitation and filtration is defined by the number of cycles necessary for removal of >95% of the airborne determined particles. Said time depends on various factors including the type of contamination and temperature, preferably the time does not to exceed 30 minutes, more preferably the time is less than 5 minutes.

This complete disinfection process continues until safe values for normal use of the facility or equipment has been reached. The full time of disinfection can vary, but is preferably from 60 to 90 minutes. The time is calculated to be safe time for a complete disinfection.

In a preferred embodiment of the present invention it can be an advantage to have a mobile disinfection unit for disinfecting the facility or equipment, where the mobile disinfection unit comprises

- at least one first inlet tube arranged for intake of air from the facility or equipment for the treatment step,
- at least one second inlet tube arranged for intake of air from the facility or equipment for the removal step,
- at least one outlet tube arranged for communicating with the at least one first and/or second inlet tube,
- a water tank in communication with the at least one outlet tube,
- means for producing ozone in communication with the at least one outlet tube,
- at least one sensor for detecting at least one parameter in the facility or equipment, said parameter is selected from the group of ozone concentration, temperature, relative humidity, concentration of one or more contaminants, and any combination of said parameters,
- means for automatically controlling the operation of the mobile disinfection unit,
- and that said at least one second inlet tube comprises a catalytic converter device arranged for decomposing ozone, a VOC filter arranged for removing bacterial viruses and other contaminants and an electrostatic filter arranged for removing molecules, particles, droplets, smoke and dust.

It is a considerable advantage if the mobile disinfection unit comprises a catalytic converter device arranged for decomposing ozone, a VOC filter arranged for removing bacterial viruses and other contaminants and an electrostatic filter arranged for removing molecules, particles, droplets, smoke and dust. The electrostatic filter can preferably be combined with electrostatic plates for providing the remaining molecules, particles and droplets with an electric charge, and an electrostatic precipitator for removal of the charged molecules, particles and droplets. The catalytic converter device is as described previously a preferred step for removal of residual ozone. The use secures that the ozone is removed thus avoiding hazardous concentrations of residual ozone being left in the facility or equipment for harming the personnel. The VOC filter and the electrostatic plates, precipitator and filter are very useful for removing contaminants left untouched by the treatment process. It is very preferable that these contaminants are also removed and not just the ozone, as the personnel first entering the facility after the disinfection process has completed otherwise would be exposed to the contaminants at a relatively high concentration present before the facility or equipment has been properly ventilated.

It is advantageous if the mobile disinfection unit comprises means for circulating air from either the at least first or second inlet opening to the at least one outlet opening. Preferably, said means for circulating air is an air blower placed in the at least one outlet tube as this provides a simple and economical unit. However, other means for circulating the air as well as other locations of said means for circulating air is also contemplated within the scope of the present invention. Circulating the air in the facility or equipment from the at least one first inlet tube to the at least one outlet tube also secures that the exact concentration of ozone can be monitored by an ozone sensor continuously, instead of just measuring the ozone concentration in the vicinity of the mobile disinfection unit without circulating the air, which would give a not precise value. The means for circulating the air to be cleaned also facilitates that the ozone and the steam/water droplets are being expelled with a high speed into the facility or equipment, thus reducing the treatment time.

The mobile disinfection unit may further comprise at least one valve arranged for controlling the communicating between the at least one outlet tube and either the at least one first or second inlet tube. The valve can facilitate that the treatment and the removal process are separated completely from each other, and thus e.g. not risk decomposing some of the ozone during the treatment process. The valve may also simplify the structure of the mobile disinfection unit, as less tubing is required. In a simple and inexpensive embodiment a motor valve is used, however other valves for opening and closing the flow between the at least one first and second inlet tube and the at least one outlet tube is also contemplated within the scope of the present invention.

It is preferred that the water tank is arranged for providing steam and/or water droplets to the at least one outlet tube. As described earlier the steam and/or water droplets can be produced by e.g. heating water, miniature spray nozzles or through high frequency shakers. Providing the water in this form ensures that the humidity is increased quickly in the facility or equipment, which is relevant as the humidity is important for conglomeration and rapid disinfection. Moreover, providing steam/water droplets to the at least one outlet tube instead of liquid water facilitates faster mixing with the ozone prior to being expelled to the facility or equipment.

The water tank can furthermore be arranged to run on either tap water or ionized water dependent on the type and level of contaminants and the water source on hand. The ionized water may have a high pH, preferably a pH around 9-10. Test has shown that ionized water with a high pH results in a faster and better decomposition of the contaminants. The mobile disinfection unit thus provide an extra flexibility in terms of locations to be operated, and in the case where tap water is used, reduces costs.

In one embodiment the mobile disinfection unit may comprise a condensation device (dehumidifier). Advantageously, the condensation device is installed in the at least second inlet tube. Said condensation device may be arranged for condensing the steam and/or water droplets remaining in the facility or equipment after the treatment and removal processes, and for storing said condensed steam and/or water droplets in the water tank. The water collected by said condensation device can thus be reused in a new disinfection process, resulting in lower costs, simpler operation and a quicker use of the facility or equipment after operation, as the humidity has been removed during the disinfection process, and does thus not have to be removed by e.g. opening a window or restarting a ventilation to the facility or equipment after the disinfection process.

It is advantageous that the means for controlling the operation of the mobile disinfection unit is a Programmable Logic Controller (PLC). The PLC gives the operator of the mobile disinfection unit the possibility of running the treatment and removal processes automatically in continuation. The mobile disinfection unit can thus be programmed to firstly run the treatment step for the time necessary until a predefined ozone concentration has existed for a predefined time interval and afterwards run the removal step, while the operator simply follows the disinfection process, e.g. on a carry-on computer, in safety outside the facility. However, other means for controlling the unit is also contemplated within the scope of the present invention.

It is further advantageous that the at least one outlet tube is arranged for communicating with the first or second inlet tube in a three-way tube system. Having the at least one outlet tube arranged for communicating with either the first or second inlet tube facilitates that the treatment process can be separated from the removal process. In the treatment process the aim is to expel e.g. ozone to the facility or equipment to react with the contaminants, where as in the removal process the aim is to remove the residual ozone and the contaminants. By separating the inlet flow of the air in two separate tubes the risk of accidentally removing e.g. ozone from the air flow prior to a complete decomposition of the contaminants is eliminated.

In an embodiment it can be an advantage if the mobile disinfection unit comprises two separated tube systems. I.e. two tube systems characterized in that a first outlet tube is arranged for communicating with the first inlet tube and a second outlet tube is arranged for communicating with the second inlet tube. This way having two completely separated tube systems ensures complete separation of the treatment process from the removal process. Furthermore, in case one of the tube systems needs repair the other tube system is thus not effected. Moreover, having two separated tube systems facilitates that the features used in the treatment process can be placed at a distance from the components used in the removal process. That could be an advantage if the mobile disinfection unit has to be used in a facility or equipment with dimensions which requires special dimensions by the mobile disinfection unit, special dimensions which can only be obtained by separating the components used in the treatment process from the components used in the removal process.

Preferably, the catalytic converter device and the VOC filter both have a honeycombed shape (hexagonal shape), as the honeycombed shape reduces the total pressure drop. The lower pressure drop results in that the total energy consumption used by the mobile disinfection unit is reduced, thus reducing the expenses for operation.

In another embodiment the mobile disinfection unit can be placed in a ducting system connected to the facility or equipment to be disinfected. The mobile disinfection unit can thus disinfect both the facility or equipment and the ducting system. The mobile disinfection unit can be placed at a central point in the ducting system, and the produced ozone and steam and/or water droplets will then be transported in the ducting system to the facility or equipment. After the treatment process has completed, the removal process will remove residual ozone and contaminates.

BRIEF DESCRIPTION OF THE DRAWINGS

The method of carrying out the present invention and the structure of the preferred mobile disinfection unit for being used in the method will be described in more detail below with references to exemplary embodiments shown in the drawings, wherein.

DETAILED DESCRIPTION OF THE INVENTION

In the figures the mobile disinfection unit is shown and described having a square shape. However, it should be understood that other shapes, such as sphere, many-sided and triangular shapes are also intended within the scope of the present invention. Furthermore, the person skilled in the art will understand that the illustrated combination of the different parts of the mobile disinfection unit is not to be understood as exhaustive and that the combination can be formed in many different ways.

Figure 1:
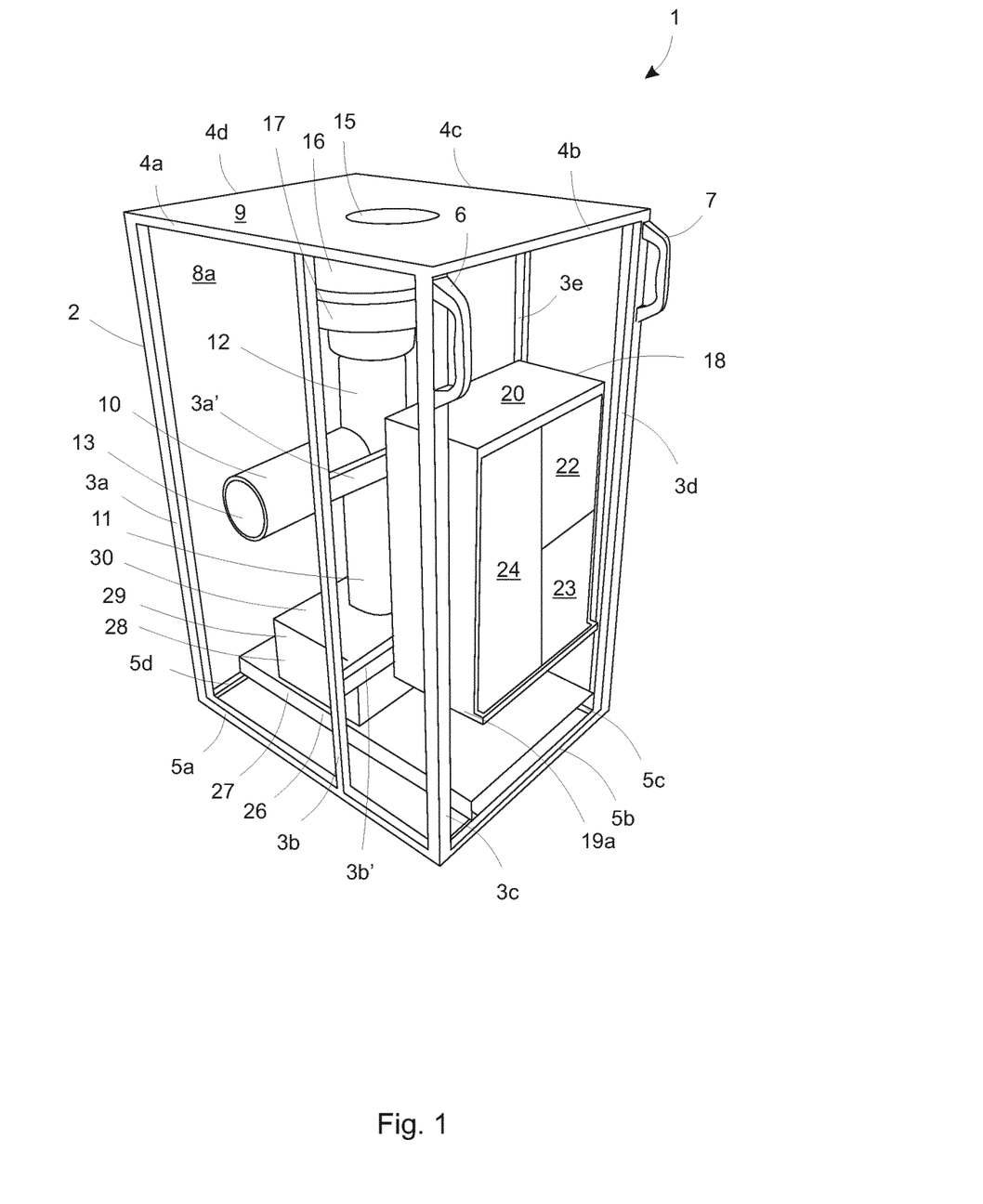
FIG. 1 shows a perspective view of the preferred embodiment of the mobile disinfection unit with three side panels removed.

FIG. 1 shows a perspective view of the preferred embodiment of the mobile disinfection unit 1. The mobile disinfection unit 1 has an outer body with a square shape. The outer body comprises a square frame 2, for supporting the different parts of the mobile disinfection unit 1. Said frame is preferably made of metal or plastic, and in the embodiment shown comprises six vertically extending rod members $3a,3b,3c,3d,3e,3f$ ($3f$ not shown) and two horizontally extending rod members $3a',3b'$ supporting four upper horizontally extending rod members $4a,4b,4c,4d$, which together form a square, and four lower horizontally extending rod members $5a,5b,5c,5d$, also forming a square. A first 6 and a second 7 handle may be positioned on the uppermost end of the rod members $3c$ and $3d$ to facilitate moving the mobile disinfection unit 1. The square frame 2 carries four side panels $8a,8b,8c,8d$ ($8b,8c,8d$ has been removed for clarity) and a top panel 9. Said panels will ensure that the unit according to the invention appears as a closed integrated unit.

Inside the square frame 2 a three-way tube system is placed. The three-way tube system is composed of a first 10 and second inlet tube 11 and an outlet tube 12. The first inlet tube 10 is arranged for intake of air from the facility or equipment, and has in one end a first inlet opening 13, penetrating one side panel $8b$ for opening to the surrounding air. The second inlet tube 11 is arranged for intake of air to be cleaned from the facility or equipment, and has a second inlet opening 14 (not shown) for opening to the surrounding air. The outlet tube 12 is connected to either the first 10 or second inlet tube 11, by use of a valve 31 (not shown), preferably a motor valve, placed in the tube crossing of the three-way tube system. The outlet tube 12 has an outlet opening 15, penetrating the top panel 9 for opening to the surrounding air.

In the outlet tube 12 an air blower 16 is placed. The air blower 16 circulates the air from the surroundings through either the first inlet opening 13 to the outlet opening 15, or through the second inlet opening 14 to the outlet opening 15, depending on whether a treatment process or a removal process is carried out.

Charged metallic plates 17 can also be placed in the outlet tube 12 for adding negative ions or electrical charge to the flow.

A square box 18 mounted on the two horizontally extending rod members $3a',3b'$ comprises four side panels $19a,19b,19c,19d$ ($19b,19c,19d$ not shown), a top panel 20 and a bottom panel 21 (not shown). The square box 18 is divided into to three parts. The first part comprises a water tank 22, which is connected to the outlet tube 12, thus providing steam and/or water droplets to the air flowing in the outlet tube 12. The second part comprises a means for producing ozone 23. The means for producing ozone 23 is in connected to the outlet tube 12, this way able to provide ozone to the air flowing in the outlet tube 12. In the third part of the square box 18 a PLC 24 is installed for automatically controlling the treatment process, e.g. the addition of steam/water droplets and ozone to the air flow dependent on the ozone concentration, and the removal process. The PLC can be monitored from a computer placed outside the facility or equipment.

Adjacent the second inlet opening 14 a sensor 25 (not shown) for monitoring the ozone concentration is placed. The monitoring of ozone concentration is used for controlling the emission of humidity and ozone to the facility or equipment and for calculating the total treatment and disinfection time.

In connection with the second inlet tube 11, firstly a catalytic converter device 26 is installed, arranged for removing residual ozone after the treatment process. Following the catalytic converter device 26 a VOC filter 27 removes bacterial viruses and other contaminants. The flow is hereafter exposed to electrostatic plates 28 thus providing the remaining molecules, particles and droplets with an electric charge, which charged molecules, particles and droplets are removed in an electrostatic precipitator 29. Finally, the remaining smaller particles are removed in an electrostatic filter 30 comprising charged metallic plates.

Figure 2:
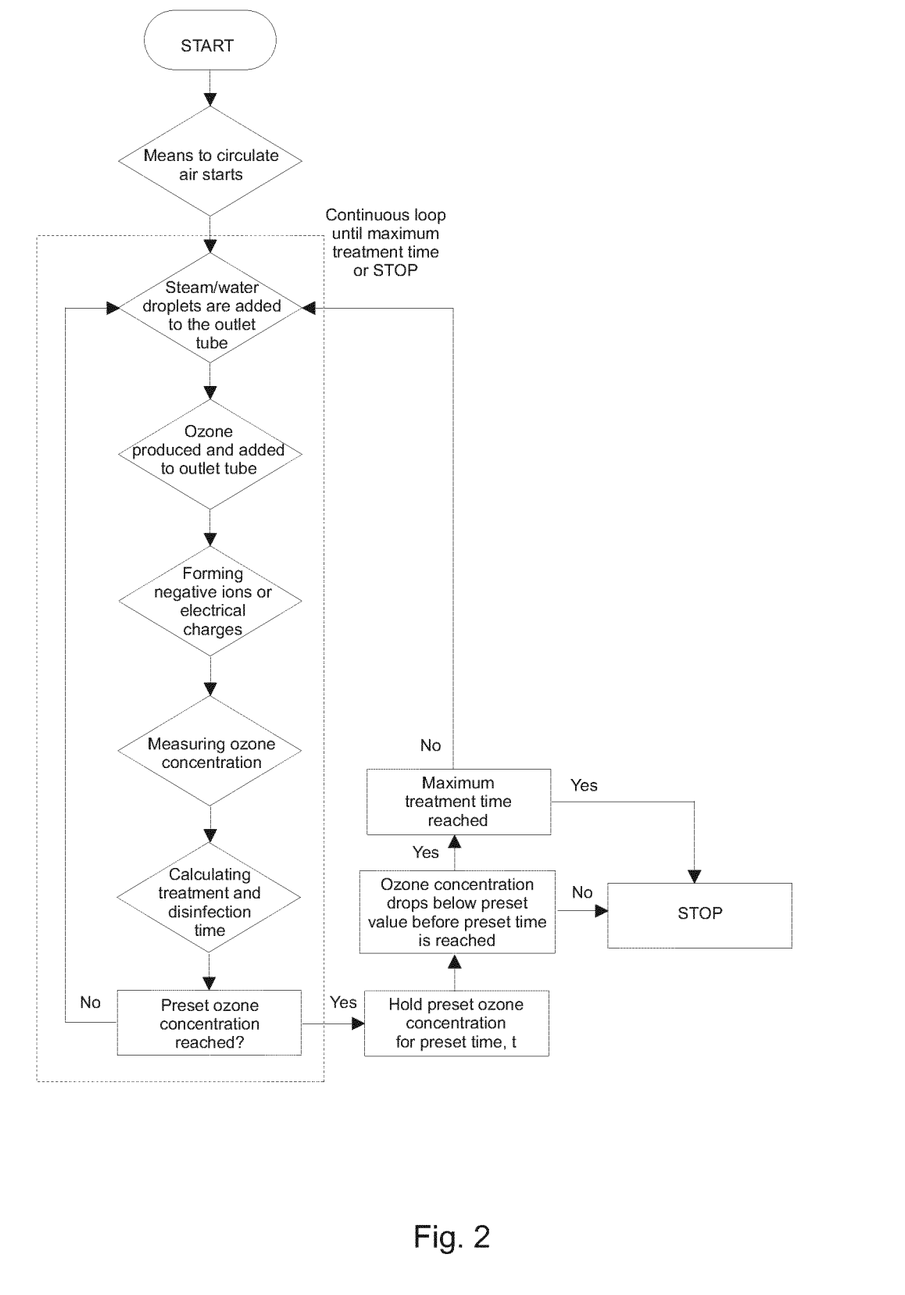
FIG. 2 shows a flow charge diagram for carrying out the treatment process.

FIG. 2 shows a flow charge diagram for carrying out the treatment process. After starting the treatment process, the means to circulate the air 16 is initiated and the air flows from the first inlet tube 10 to the outlet tube 12. The means to circulate air 16 is preferably running for the entire treatment process. Now a number of steps running in a continuous loop begins. The steps do not necessarily start simultaneously, however preferably they do. The steps comprise adding steam and/or water droplets and ozone to the outlet tube 12. However, before being expelled to the surrounding air the flow is added negative ions or an electrical charge. During the entire treatment process a sensor 25 measures the ozone concentration in the facility or equipment, thus providing an input to the PLC 24 for calculating the disinfection and treatment time, which can be monitored by the operator on a computer placed outside the facility or equipment. As long as the predefined ozone concentration has not yet been reached the loop continues. The predefined ozone concentration can in a preferred embodiment be 15 ppm. When the predefined ozone concentration is obtained, the predefined ozone concentration must be kept for a predefined time, t, which in the present case is 45 minutes, i.e. when the ozone concentration is 15 ppm. In case the ozone concentration drops below the predefined value before t is reached, the PLC 24 ensures that the ozone concentration rises again. After iteration of the described steps a certain number of times, the predefined ozone concentration has been kept for the time t and the treatment process stops unless the treatment time exceeds a predefined maximum treatment time. In this case the treatment process is stopped before complete disinfection.

Figure 3:
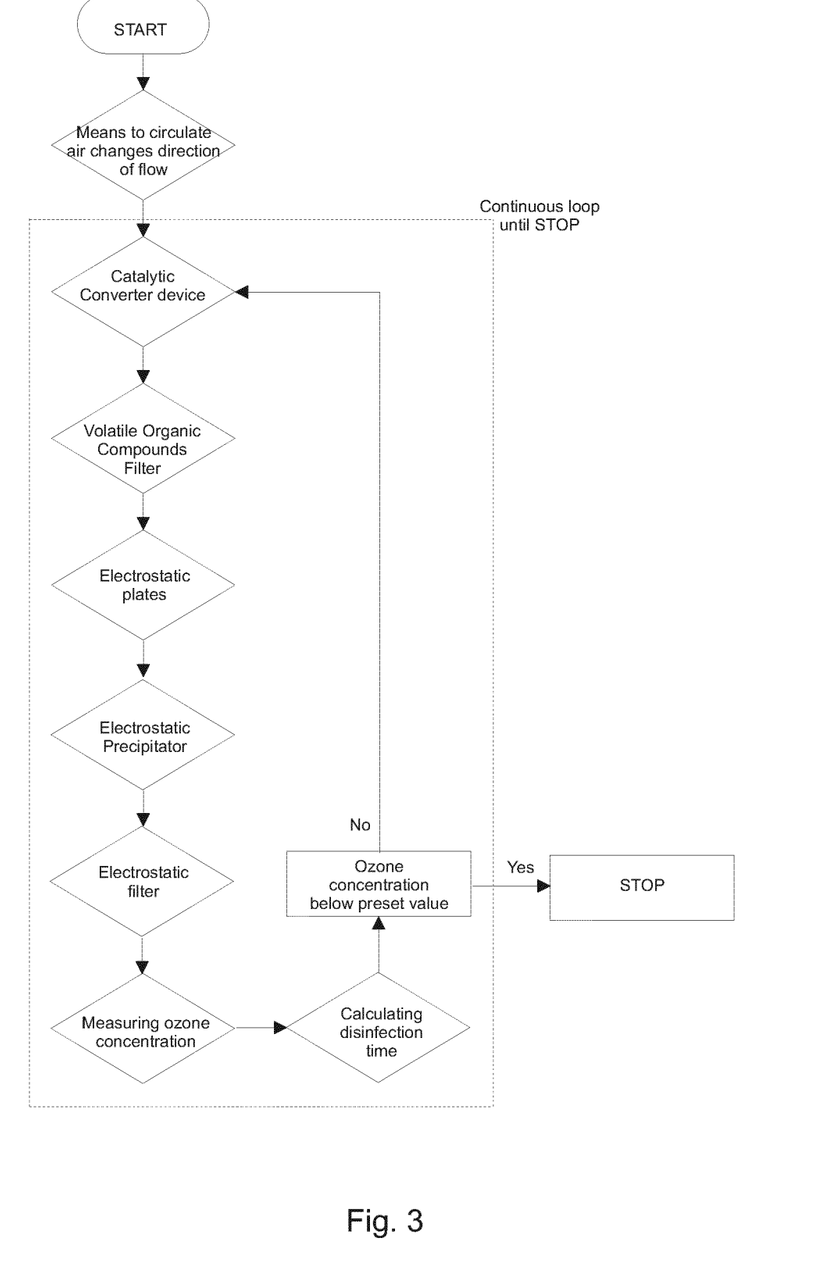
FIG. 3 shows a flow charge diagram for carrying out the removal process.

FIG. 3 shows a flow charge diagram for carrying out the removal process. After starting the removal process, the means to circulate the air 16, e.g. air blower 16, is initiated and changes the direction of the air to flow from the second inlet tube 11 to the outlet tube 12. The means to circulate the air 16 is running for the entire removal process. As is the case for the treatment process, a number of steps running in a continuous loop begins. The steps comprises first exposing the air to be cleaned to a catalytic converter device 26, thus removing residual ozone. After the catalytic converter device 26, a VOC filter 27 removes bacterial viruses and other contaminants. The remaining molecules, particles, droplets and smaller particles are removed by a combination of the electrostatic plates 28, the electrostatic precipitator 29 and the electrostatic filter 30. During the entire treatment process a sensor 25 measures the ozone concentration in the facility or equipment, thus providing an input to the PLC 24 for calculating the disinfection time, which can be monitored by the operator on a computer placed outside the facility or equipment. As long as the ozone concentration is not below a predefined lower value, the loop continues. After the predefined lower value has been reached the removal process stops.

The unit and method according to the invention has a simple and inexpensive design, and can therefore be used equally well for both private and in medical or hospital facilities where known disinfection units are too troublesome and complicated to use.

Modifications and combinations of the above principles and designs are foreseen within the scope of the present invention.

What is claimed is:

1. A mobile disinfection unit for disinfecting a given facility or equipment, the mobile disinfection unit comprising:
    at least one first inlet tube arranged for intake of air from the facility or equipment for treatment,
    at least one second inlet tube arranged for intake of air from the facility or equipment for removal,
    at least one outlet tube selectively associated and arranged for communicating with either of the at least one first or second inlet tubes,
    a water tank in communication with the at least one outlet tube,
    means for producing ozone in communication with the at least one outlet tube with or without means for adding negative ions or electrical charge to the air,
    at least one sensor for detecting at least one parameter in the facility or equipment, said parameter selected from the group consisting of ozone concentration, temperature, relative humidity, concentration of one or more contaminants, or a combination thereof, and
    means for controlling the operation of the mobile disinfection unit to selectively conduct a treatment step using ozone for disinfection, a removal step for removing particles, or both in sequence,
    wherein the at least one second inlet tube comprises a catalytic converter device arranged for decomposing ozone, a Volatile Organic Compounds (VOC) filter arranged for removing bacterial viruses and other contaminants, and an electrostatic filter arranged for removing molecules, particles, droplets, smoke and dust from the air during the removal;
    wherein the communication between the at least one outlet tube and either of the first or second inlet tube is controlled so that air cannot flow through both the first and second inlet tubes at the same time; and
    wherein the first inlet tube connects to a flow path between the second inlet tube and the outlet tube.

2. The mobile disinfection unit of claim 1, further comprising electrostatic plates for providing the remaining molecules, particles and droplets with an electric charge, and an electrostatic precipitator for removal of the charged molecules, particles and droplets.

3. The mobile disinfection unit of claim 1, further comprising means for circulating air from either at least one inlet opening to at least one outlet opening.

4. The mobile disinfection unit of claim 3, wherein the means for circulating air is an air blower placed in the at least one outlet tube.

5. The mobile disinfection unit of claim 1, further comprising at least one valve arranged for controlling communicating between the at least one outlet tube and either the first or second inlet tube.

6. The mobile disinfection unit of claim 1, wherein the water tank is arranged for providing steam or water droplets to the at least one outlet tube.

7. The mobile disinfection unit of claim 1, wherein the water tank can run on either tap water or ionized water.

8. The mobile disinfection unit of claim 1, wherein the means for controlling operation of the mobile disinfection unit is a Programmable Logic Controller (PLC).

9. The mobile disinfection unit of claim 1, wherein a relative humidity level above 50% at room temperature is applied to the facility or equipment.

10. The mobile disinfection unit of claim 1, wherein the at least one outlet tube is arranged for communicating with the first or second inlet tube in a three-way tube system.

11. The mobile disinfection unit of claim 1, wherein a first outlet tube is arranged for communicating with the first inlet tube and a second outlet tube is arranged for communicating with the second inlet tube.

12. The mobile disinfection unit of claim 1, wherein the catalytic converter device or the VOC filter has a honeycombed shape.

13. The mobile disinfection unit of claim 1, further comprising at least one valve arranged for controlling the communicating between the at least one outlet tube and either the at least one first or second inlet tube for separating conducting of the treatment and removal.

14. The mobile disinfection unit of claim 13, wherein the at least one valve is a motor valve.

15. A method of disinfecting a given facility or equipment such as a room, apparatus, container or vehicle, by means of a mobile disinfection unit, which method comprises:
    a treatment step arranged for adding ozone along with steam or water droplets into the air of the facility or equipment,
    continuously detecting the ozone concentration in the facility or equipment,
    a removal step arranged for removing residual ozone and contaminates including end- and by-products present after the treatment step as well as inorganic material, organic compounds and organisms from air removed from the facility or equipment when a predefined ozone concentration has been reached and is maintained for a specific time interval,
    wherein the mobile disinfection unit comprises:
        at least one first inlet tube arranged for intake of air from the facility or equipment for treatment,
        at least one second inlet tube associated and arranged for intake of air from the facility or equipment for removal,
        at least outlet tube selectively associated and arranged for communicating with either of the at least one of the first or second inlet tubes,
        a water tank in communication with the at least one outlet tube,
        means for producing ozone in communication with the at least one outlet tube with or without means for adding negative ions or electrical charge to the air, at least one sensor for detecting at least one parameter in the facility or equipment, said parameter selected from the group consisting of ozone concentration, temperature, relative humidity, concentration of one or more contaminants, or a combination thereof, and means for controlling the operation of the mobile disinfection unit to selectively conduct a treatment step using ozone for disinfection, a removal step for removing particles, or both in sequence, wherein the at least one second inlet tube comprises a catalytic converter device arranged for decomposing ozone, a Volatile Organic Compounds (VOC) filter arranged for removing bacterial viruses and other contaminants, and an electrostatic filter arranged for removing molecules, particles, droplets, smoke and dust from the air during the removal;

wherein the communication between the at least one outlet tube and either of the first or second inlet tube is controlled so that air cannot flow through both the first and second inlet tubes at the same time; and wherein the first inlet tube connects to a flow path between the second inlet tube and the outlet tube.

16. The method according to claim 15, which further comprises continuously detecting an additional parameter in the facility or equipment, with the parameter selected from the group consisting of temperature, relative humidity, concentration of one or more contaminants, or a combination of these parameters.

17. The method according to claim 15, wherein the treatment step comprises:

circulating air to flow from the first inlet opening to an outlet opening, producing steam or water droplets and adding the steam or water droplets to the flow of air for facilitating the formation of hydroxyl radicals, producing and mixing ozone molecules with the steam or water droplets in the flow of air while optionally adding negative ions or electrical charge to the mixture, releasing the mixture to the facility or equipment, calculating a treatment and disinfection time, adjusting either the steam/water droplet and ozone concentrations to meet the calculated treatment time, or adjusting the treatment time if the predefined ozone level cannot be reached in the calculated treatment time, stopping production and release of steam/water droplets and ozone to the facility or equipment after the treatment time has elapsed.

18. The method according to claim 15, wherein the removal step includes:

in a first step circulating air to flow from an inlet opening to an outlet opening, in a second step exposing the inlet flow to the catalytic converter device with the device comprising one or more ozone removal catalysts for removal of residual ozone, in a third step exposing the flow to the VOC filter with the VOC filter being composed of titanium dioxide irradiated with Ultra Violet (UV) radiation for removal of bacterial viruses and other contaminants, in a fourth step exposing the flow to electrostatic plates thus providing the remaining molecules, particles and droplets with an electric charge, in a fifth step exposing the flow to an electrostatic precipitator for removal of the charged molecules, particles and droplets, and in a sixth step exposing the flow to an electrostatic filter comprising charged metallic plates for removal of any remaining smaller particles.

* * * * *